United States Patent [19]
Jacquier et al.

[11] Patent Number: 5,281,750
[45] Date of Patent: Jan. 25, 1994

[54] CHIRAL POLYMERS FOR THE PRODUCTION OF EXCESS ENANTIOMERS

[75] Inventors: Robert Jacquier; Monique Calmes; Jacques Daunis, all of Montpeller, France

[73] Assignee: Rhone-Poulenc Chimie, Courbevoie, France

[21] Appl. No.: 976,672

[22] Filed: Nov. 16, 1992

Related U.S. Application Data

[63] Continuation of Ser. No. 636,476, Dec. 31, 1990, abandoned, which is a continuation-in-part of Ser. No. 545,526, Jun. 29, 1990, abandoned.

[30] Foreign Application Priority Data

Jun. 29, 1989 [FR] France ................. 89 08679

[51] Int. Cl.$^5$ ............... C07B 57/00; C07B 55/00; C07B 53/00; C07C 227/30
[52] U.S. Cl. ................... 562/401; 562/445; 562/554; 562/575; 562/553; 564/302; 564/303; 564/304; 526/263; 526/304; 526/305; 526/306; 525/326.7; 525/328.3; 525/359.5; 525/359.6; 525/374; 525/375; 525/379
[58] Field of Search ............ 526/263, 304, 305, 306; 525/326.7, 328.3, 359.5, 359.6, 374, 375, 379; 562/401, 402; 564/302, 303, 304

[56] References Cited

FOREIGN PATENT DOCUMENTS 0300448 1/1989 European Pat. Off. .
2515645 5/1983 France .

OTHER PUBLICATIONS

Calmes et al., Tetrahedron, 46:6021–6032 (1990).
Pine et al., Organic Chemistry, Fourth Edition, McGraw-Hill Book Company, New York, 1980, pp. 567–569.
M. Calmes et al., "Polyacrylic Crosslinked Resins With Pendant Chirality As Auxiliary In Supported Asymmetric Synthesis," Tetrahedron Letters, Pergamon Journal, 27(36):4303–4306 (1986).
McArthur et al., "Polymer Supported Enantioselective Reactions.III.Protonation of Lithioenamine Derivatives of Racemic 2-Methylcyclohexanone," Can. J. Chem. 60:2984–45 (1982).
Frechet et al., "Polymer Assisted Asymmetric Reactions.II.*Synthesis and Application of a Crosslinked Resin Containing (R)14 1-(4-Vinylphenyl)Ethylamine," Reactive Polymers, 227–235 (1982).
Peter Marfey, "Determination of d-Amino Acids-.II.Use of a Bifunctional Reagent, 1,5-Difluoro-2,-4-Dinitrobenzene", Carlsberg Res. Commun., 49:591–596 (1984).
Colwell et al., "Synthesis of Carboxylic Acids and Esters Using Polymer-Bound Oxazolines," J. Org. Chem., 46:3097–3102 (1981).
Kawana et al., "Asymmetric Synthesis with Sugar Derivatives. V.$^{1,2}$) The Synthesis of α-Hydroxy Acids on Insoluble Polymer Supports," Bull. Chem. Soc. Japan, 47:160–165 (1974).
McArthur et al., "Polymer Supported Enantioselective Reactions.II. α-Methylation of Cyclohexanone", Can. J. Chem., 60:1836–1841 (1982).

Primary Examiner—Joseph L. Schofer
Assistant Examiner—Mark Nagumo
Attorney, Agent, or Firm—Finnegan, Henderson, Farabow, Garrett & Dunner

[57] ABSTRACT

The present invention relates to chiral supports and to their use in the asymmetric synthesis, deracemization and optical inversion of organic chiral compounds. In particular, the supports are used in combination with thermal equilibration of a species having a reactive achiral portion. Preferably, these supports are obtained by the copolymerization of at least one chiral unit and at least one functionalizing unit or by the polymerization of at least one chiral unit which is a source of said functionalizing unit. Optionally, a crosslinking agent is utilized. By utilizing these supports and thermal equilibration, excess enantiomers can be produced.

64 Claims, No Drawings

CHIRAL POLYMERS FOR THE PRODUCTION OF EXCESS ENANTIOMERS

This application is a continuation of application Ser. No 07/636,476, filed Dec. 31, 1990, now abandoned, which is a continuation-in-part of Ser. No. 07/545,526, filed Jun. 29, 1990, abandoned.

The present invention relates to reusable chiral polymers permitting the supramolecular asymmetric synthesis, on a support, of compounds having chiral centers. It relates as well to new thermodynamically equilibrated processes for the synthesis of excess enantiomers by deracemization and optical inverison.

There are few examples in the prior art of asymmetric syntheses supported on a polymer. Their principle remains the same as in solution, requiring the presence of a chiral auxiliary in proximity to the prochiral center. Utilizing polystyrene supports in all cases, these examples relate to asymmetric syntheses of hydroxy acids (Kawana and Emotz, Bull. Chem. Soc. Japan, 47:160 (1974); of arylaliphatic esters (McManus et al., J. Org. Chem. 46: 3097 (1981) and of 2-methylcyclohexanone (Leznoff et al., Canad. J. Chem. 60: 1836 (1986); Frechet et al., Reactive Polymers, 1983, 1, 227). However, if the work of Leznoff et al. (loc. cit.) is excepted, the enantiomeric excesses remain average (56-62%). Finally, Leznoff et al. (Canad. J. Chem., 1982, 60, 2984) carried out the asymmetric protonation of the lithium enamine of racemic 2-methylcyclohexanone anchored to a chiral arm grafted onto a polystyrene. Leznoff's asymmetric supported synthesis is based on the general principle that asymmetric induction is the result of the presence of a chiral center closely bound to the prochiral carbon atom.

Another strategy consists in utilizing a chiral polyacrylic support producing a supramolecular asymmetric induction (Calmes, Daunis, Jacquier, Nkusi, Verducci and Viallefont, Tetrahedron Letters, 1986, 27, 4303). However, when this strategy was applied to the synthesis of amino acids, it was thought to be necessary to work at a very low temperature ($-78°$ C.) in order to enhance the stability of the enolates via kinetic control. Under these conditions, in the synthesis of amino acids, enantiomeric excesses did not exceed 63% in alkylations of enolates carried out at $-78°$ C.

SUMMARY OF THE INVENTION

The present invention relates to a process for producing an excess of enantiomers comprising the steps of reversibly reacting a starting material selected from a prochiral derivative, a mixture of enantiomers or a substantially optically pure enantiomer with at least one functionalizing unit, preferably achiral, of a support obtained by the polymerization of at least one chiral unit which is also the source of a functionalizing unit thereby creating a second species having a reactive achiral portion. This species is equilibrated thermodynamically and an asymmetric carbon atom is created from the reactive achiral portion of said species. The second species containing the asymmetric carbon atom, which is present in enantiomeric excess, is then separated from the polymeric support.

In another embodiment of the invention, at least one thermodynamically equilibrated achiral species is obtained by converting to an achiral portion (1) the prochiral portion of a prochiral derivative or (2) the chiral portion of at least one compound selected from a racemic mixture of enantiomers and a substantially optically pure enantiomer, said prochiral derivative or said compound having been reversibly reacted with at least one functionalizing unit of a support, said support having been obtained by the copolymerization of at least one chiral unit and at least one functionalizing unit or by the polymerization of at least one chiral unit which is a source of said functionalizing unit, and wherein said thermodynamically equilibrated achiral species enables the production of an enantiomeric excess in a process for producing enantiomers.

The present invention also relates to the development of a copolymer having a pendant chirality which enables the production of enantiomeric excesses through processes such as asymmetric synthesis, deracemization and optical inversion. A further aspect of the present invention is the realization that a specific enantiomer can be better obtained by processing polymer-supported prochiral compounds at higher temperatures using thermodynamic equilibration than at the very low temperatures necessary for kinetic control as described in the prior art.

The support of the present invention can be obtained by polymerization as well as copolymerization. Preferably, the support of the present invention is a copolymer obtained, in particular, by the free-radical copolymerization of a chiral unit selected from monomer, oligomer, or prepolymer, with a functionalizing unit, preferably achiral, and optionally, but preferably with a cross-linking unit. The copolymerization of the chiral unit and functionalizing unit can take place in the presence of the cross-linking unit in a one step process or copolymerization can take place prior to crosslinking in a two-step process.

It is also envisaged that a chiral unit can also be the source of a functionalizing unit. Polymerization of such a chiral unit can be carried out in the presence of at least one cross-linking unit or in a sequential process where the crosslinking unit is added after polymerization.

It is further contemplated that where the chiral unit is a oligomer or prepolymer, the chiral unit can be the source of the crosslinking unit as well as the functional unit.

The invention further consists in new processes for carrying out the reactions of synthesis, inversion or racemization on the polymer according to the present invention, thereby enabling substantially pure, preferably optically pure, active compounds to be obtained and permitting deracemization or inversion according to techniques which usually permit racemization.

In a preferrred embodiment of the present invention, as shown in FIG. 1,

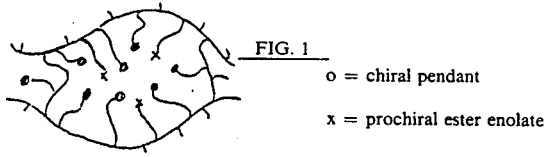

FIG. 1
o = chiral pendant
x = prochiral ester enolate a polymer can be designed in which chiral pendants surround a prochiral enolate, such as lithium ester enolate, the latter being covalently and reversibly linked or anchored to the polymer chain via reaction with an achiral arm. As a result, the whole polymer can act as a chiral auxiliary and supramolecular asymmetric induction can occur. Moreover, proximity effects and complexation between the prochiral enolate, such as lithium enolate and the pendant functional group can also reinforce the stereoselectivity by providing transition-state rigidity and increased thermal stability. Increased thermal stability can allow thermodynamic equilibration at relatively high temperatures with concomitant increase in enantioselectivity.

Thus, one of the objects of the present invention is to provide a family of polymers which can be utilized for asymmetric synthesis, deracemization or optical inversion, all of which can be carried out with enhanced enantiomeric selectivity.

Therefore, an additional object of the present invention is to provide processes for asymmetric synthesis, deracemization or optical inversion which enable the production of an enantiomeric excess.

In the present invention, the process for asymmetric synthesis comprises the steps of reversibly reacting (1) a prochiral derivative or (2) at least one enantiomer with a functionalizing unit of a support polymerized from at least one chiral unit, wherein said chiral unit may also be the source of said functionalizing unit or copolymerized from at least one chiral unit and at least one functionalizing unit;

converting the prochiral portion of said reacted prochiral derivative or the chiral portion of said enantiomer into a species having a reactive achiral portion;

equilibrating thermodynamically said species having said reactive achiral portion;

creating an asymmetric carbon atom from the reactive achiral portion of said species; and separating a second species containing said asymmetric carbon atom from said polymeric support, wherein said second species is present in enantiomeric excess.

The invention further encompasses a process for deracemization comprising the steps of reversibly reacting a racemic mixture of enantiomers with at least two functionalizing units of a copolymeric support obtained by the copolymerization of at least one chiral unit with at least one functionalizing unit or of a polymeric support obtained by the polymerization of at least one chiral unit which is also the source of said functionalizing unit;

converting the chiral portion of each of said enantiomers reacted with said functionalizing units into a species having a reactive achiral portion;

equilibrating thermodynamically said species having said reactive achiral portion;

creating an asymmetric carbon atom from the reactive achiral portion of said species; and separating a second species containing an asymmetric carbon atom from said copolymeric or polymeric support, wherein said second species is present in enantiomeric excess.

Another aspect of the present invention is a process for inversion of enantiomer configuration comprising the steps of reversibly reacting an enantiomer of arbitrary configuration with a functionalizing unit of a copolymeric support obtained by the copolymerization of at least one chiral unit with at least one functionalizing unit or a polymeric support obtained by the polymerization of at least one chiral unit which is also the source of said functionalizing unit;

converting the chiral portion of said enantiomer reacted with said functionalizing unit into a species having a reactive achiral portion;

equilibrating thermodynamically said species having said reactive achiral portion;

creating an asymmetric carbon atom from the reactive achiral portion of said species; and separating a second species containing an asymmetric carbon atom from said copolymeric or polymeric support, wherein said second species is present in enantiomeric excess and wherein said second species is an enantiomer having a configuration opposite to that of said enantiomer of arbitrary configuration.

The invention also encompasses a second asymmetric carbon-containing species formed from a thermodynamically equilibrated first species having a reactive achiral portion, said first species having been formed by (1) converting the prochiral portion of a reacted prochiral derivative or (2) by converting the chiral portion of at least one reacted enantiomer into a species having a reactive achiral portion, said prochiral derivative or said enantiomer having been reversibly reacted with a functionalizing unit of a copolymeric or polymeric support, said support having been obtained by the copolymerization of at least one chiral unit and at least one achiral functionalizing unit or by the polymerization of at least one chiral unit which is the source of said functionalizing unit.

Thermodynamic equilibration of the achiral species enables the production of an improved enantiomeric excess in a process for producing enantiomers.

The invention further encompasses a reaction product obtained by reacting reversibly a prochiral derivative with a functionalizing unit of a copolymeric or polymeric support, said support being obtained by (1) the copolymerization of at least one chiral unit and at least one functionalizing unit or (2) the polymerization of at least one chiral unit which is the source of said functionalizing unit, with the proviso that said chiral unit is not (L)-1-acryloyl 2-methoxymethylpyrrolidine.

In all of the above embodiments of the present invention utilizing a copolymer, the chiral unit of the copolymer preferably represents, expressed in moles, a large percentage of the copolymer and will vary according to the chemical properties of the chiral unit. In a non-preferred embodiment, when the chiral unit does not possess sites capable of forming intramolecular hydrogen bonds with another chiral unit, it is desirable that the chiral unit represents at least 66%, and advantageously 70%, of the total units, and preferably 75%. In a preferred embodiment, when the chiral unit possesses sites capable of forming hydrogen bonds between two chiral units, the percentage can be significantly smaller. It is, however, preferable that at least 50%, and preferably 66%, of the units are chiral.

Although it is possible to envisage units obtained by polycondensation, such as, for example, an amide unit as in polyamides or an ester unit as in polyesters, the most suitable chiral unit is a unit which can be obtained by the polymerization of chiral monomers possessing an unsaturated bond.

The chiral monomers may be obtained by the grafting of a group bearing unsaturation onto chiral groups; for example, there may be mentioned:

The monomers obtained by the amidation or esterification of acrylic acids, optionally substituted, by means of optically active molecules in which the asymmetric carbon is advantageously well exposed, as in the case where the active carbon forms part of a ring.

The coupling of the chiral derivatives with the acrylic radical to obtain a chiral monomer (as defined herein, chiral monomer means the same thing as chiral unit) may be carried out by means of an amide functional group (for example, with amino acids or their derivatives such as, for example, the amides and esters) or an ester functional group. It may also be carried out by any technique known to those skilled in the art, for example, vinyl groups may be grafted onto the aromatic rings of chiral derivatives possessing the latter, such as, for example, derivatives of phenylalanine and tryptophan and adrenaline derivatives and the like.

The chiral monomer may also be obtained by reciprocal coupling systems, such as, for example, the manufacture of enol esters from optically active acids such as amino acids, or of enol ether from an alcohol possessing an active group. It is also possible to utilize compounds possessing asymmetric carbons and a polymerizable double bond, after optical resolution where appropriate.

It is preferable that, in the chiral monomer generating the chiral unit, there be a double bond close to the asymmetric carbon. More specifically, it is preferable that the number of atoms between the double bond and the chiral center is at most equal to 5, preferably to 3, and most preferably to 2.

Moreover, the chiral unit advantageously possesses at least one functional group bearing hydrogen capable of forming hydrogen bonds with another chiral unit of the same kind with another chiral unit, preferably of the same kind. Among functional groups, acidic functional groups, alcohol functional groups including phenols, amide functional groups and amine functional groups may be mentioned.

Among chiral units usually employed in the processes of asymmetric synthesis, deracemization and optical inversion, there may be mentioned, by way of example, the acrylamides, optionally substituted in the acryloyl group, formed from the following amines:

prolinol, and optionally its derivatives in the form of esters or ethers of the alcohol functional group, such as prolinol methyl ether, 1-amino-1-phenylethanes, in particular 1-(N-methylamino)-1-phenylethane, 1-(N-alkylamino)-2-alkoxypropane in which the alkyl or alkoxy groups can represent linear or branched alkyls, preferably a methyl or a hydrogen, 1-pyrrolidinyl-2-methylpyrrolidine, N methyl-alpha-phenylethylamine, methylbenzylamine, and 1-amino-1-alkyl-2-hydroxyethane and its derivatives mono- or dimethylated on the nitrogen and on the alcohol. The derivative disubstituted on the nitrogen is excluded since it is incapable of forming an amide bond with the acryloyl group (however it could be used if an acrylic ester is utilized as a chiral monomer).

Generally speaking, it is preferable that the chiral unit be of low molecular weight, that is to say advantageously at most equal to 200, and preferably at most equal to approximately 150.

The functionalizing unit, preferably an achiral functionalizing unit, can be derived from any unit bearing protective functions as defined in works well-known to those skilled in the art, such as the work by Theodore W. Greene "Protective Groups in Organic Synthesis" published by John Wiley and Sons, 1981, and that by J. F. W. McOmie, "Protective Groups in Organic Chemistry" published by Plenum Press, London and New York, 1973, both of which are specifically incorporated by reference herein.

The protective groups may be converted to give functionalizing monomers (as defined herein, the terms functionalizing monomer and functionalizing unit are synonymous) in the same manner, when the appropriate changes are made, as can be the case also for the chiral units. Thus, anilide groups converted to acrylanilides bearing said protective groups as defined above may be used as monomer sources for the functionalizing units. Among protective groups giving the best results, aminobenzaldehyde derivatives, which are especially useful in the synthesis or deracemization of (primary) amino derivatives such as amino acids, may be mentioned. Groups which also may be mentioned include functionalization agents that have a hydroxyl (esterification), halogenate (SN2), or amine (Schiff base) anchorage point instead of an aldehyde stem.

Acryloyl derivatives (including methacryloyl derivatives), the derivatives derived by amidation with acrylic acids of the following derivatives:

$CH_3-NH-C(R_1)(R_2)-CHO$ with $R_1$ or $R_2$ aryl or aralkyl, may be mentioned.

Within the scope of the present invention, the functionalizing units can be derived from the polymerization of chiral units of the above type, but onto which the envisaged protective functions which are sources for the functionalizing units have been grafted.

It is very highly preferable that the support according to the present invention also contain crosslinking (crossbonding) units, the terms crosslinking and crossbonding being synonymous. These crossbonding units are derived from monomers in general bearing 2 unsaturated bonds. These monomers are well-known to those skilled in the art in the polymer field. Diesters or diamides of acrylic acids, obtained by the action of acroylating reagents on dialcohols or diamines, such as N,N-dimethylethylenebisacrylamide and N,N-dimethylethylene diamine, may be utilized in particular.

In those embodiments of the invention where a copolymeric support is used, the different monomers are selected according to techniques well-known to those skilled in the art so as to be compatible for the purpose of a smooth copolymerization. Copolymerization, however, is not the only criterion; it is also advisable that the monomers do not interact with one another from a chemical standpoint.

The molar percentage of the crosslinking agent is advantageously between 0 and 20% of the chiral unit, and preferably from 5 to 15%. The functionalizing unit constitutes the remainder of this functionalized chiral polymer or copolymer.

Sequences of chiral monomer may be inserted into a non-chiral polymer and still come within the scope of the present invention.

The different monomers are selected in such a way that the mass ratios, compatible with the mole ratios given above, are advantageously between 50 and 65% for the chiral unit, between 5 and 15% by weight for the crosslinking unit and between 40 and 25% for the functionalizing unit.

The synthesis of the supports according to the present invention can readily be carried out according to techniques well-known to those skilled in the art. Those techniques which are described in Examples 1 to 3 may be taken as an example of those useful in practicing the invention.

The chiral polymers according to the present invention permit asymmetric synthesis, deracemization and optical inversion, wherein a species containing an asymmetric carbon-atom is produced in enantiomeric excess. It has been found that in case of optical inversion, the optical isomer obtained can depend on the choice of the R or S form of the chiral monomer.

In the description which follows, the reactions of asymmetric synthesis, deracemization and optical inversion will be explained using amino acids as an illustration of how it is possible to synthesize enantiomers in enantiomeric excess by means of the present invention.

The subject of the present invention is, in addition, a process for the asymmetric synthesis, on a support, of amino acids, wherein said prochiral derivative is of the general formula:

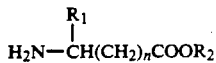
(I)

in which n is equal to 0 or 1,
$R_1$ represents a hydrogen atom, and
$R_2$ represents a linear or branched $C_1$ to $C_5$ alkyl group or an aryl group,
and wherein:
  in a first step, the prochiral portion of the prochiral derivative bonded to said polymeric support by reaction with the functionalizing unit of said support is deprotonated at room temperature with a strong base in an aprotic solvent to create a species having a reactive chiral portion;
  in a second step, either alkylation or protonation of the deprotonated prochiral derivative bonded to the chiral polymer is performed, to create an asymmetric carbon atom from the reactive chiral portion of the species; and
  in a third step, a bond connecting a second species containing said asymmetric carbon atom to the polymeric support is cleaved by hydrolysis to obtain an amino acid of general formula:

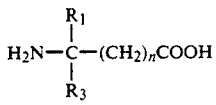
(II)

where $R_1$ and n are as defined above, $R_3$ represents an alkyl or aralkyl group, and $R_1$ and $R_3$ necessarily are different, wherein the amino acid is present in an enantiomeric excess.

In said first step, the prochiral derivative bonded to polymeric support by reaction with the achiral functioning unit is deprotonated at room temperature with a strong base, preferably an excess of strong base, in a solvent, preferably aprotic and preferably polar, such as, for example, tetrahydrofuran. In the deprotonated derivative, the orientation of the resulting carbanion is determined by the structure of the polymer and being preferably substantially rigid, it increases thermal stability and reinforces stereoselectivity, resulting in more enantiomer of either the S or R configuration than would be expected if there were no special orientation.

In a second step, the deprotonated intermediate, i.e., the reactive achiral portion of the species, is subjected to either alkylation or protonation of the deprotonated derivative bonded to the chiral polymer, so as to create or recreate an asymmetric carbon on said derivative.

In a third step, a bond connecting the polymeric support to the species containing the asymmetric carbon atom, created from the species having a reactive achiral portion, is cleaved by hydrolysis to obtain a chiral compound in enantiomeric excess. The polymer support can then be recovered and can be reused, preferably in up to ten successive operations without any loss of chemical yield or enantioselectivity.

In another aspect of the present invention, a process for the asymmetric synthesis of amino acids begins with at least one enantiomer, wherein said enantiomers are of the general formula:

(I)

in which n is equal to 0 or 1,
$R_1$ represents an alkyl or aralkyl group, and
$R_2$ represents a linear or branched $C_1$ to $C_5$ alkyl group or an aryl group,
and wherein:
  in a first step, the chiral portion of the enantiomer bonded to said polymeric support by reaction with the functionalizing unit of said support is deprotonated at room temperature with a strong base, preferably in excess, in an aprotic solvent to create a species having a reactive chiral portion;
  in a second step, either alkylation or protonation of the deprotonated enantiomer bonded to the chiral polymer is performed, to create an asymmetric carbon atom from the reactive chiral portion of the species; and
  in a third step, a bond connecting a second species containing said asymmetric carbon atom to the polymeric support is cleaved by hydrolysis to obtain an amino acid of general formula:

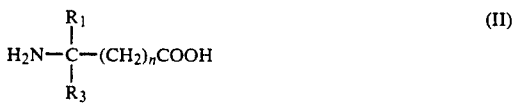
(II)

where $R_1$ and n are as defined above, $R_3$ represents an alkyl or aralkyl group, and $R_1$ and $R_3$ necessarily are different, wherein the amino acid is present in an enantiomeric excess.

In an alternate embodiment, chiral product remaining after hydrolysis with d lute hydrochloride and having the general formula:

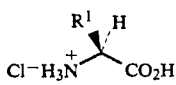

is reacted with hexamethyldisilazane (HMDS) to give the bistrimethylsilyl derivative which is further treated with methanol to allow isolation of the substantially pure amino acid, the amount of which configuration (S) or (R), will have been determined by the orientation of the carbanion of the support, preferably containing a chiral unit.

In the deprotonation step, strong bases, preferably in excess, may be used. These include, without limitation, amides such as lithium diisopropylamide (LDA) or lithium tetramethylpiperide, the lithium salt of hexamethyldisilazane, anions derived from alkanes, such as butyllithium, and alcoholates such as potassium tert-butylate. It has also been demonstrated that it is preferable to anionize all of the polymer's acid protons with an excess of LDA to achieve the best enantioselectivity.

According to a preferred embodiment of the process according to the present invention, protonation of the deprotonated derivative bonded to the chiral polymer is performed by adding water, an alcohol or an inorganic or organic acid.

According to a further preferred embodiment of the process according to the present invention, alkylation of the deprotonated derivative bonded to the chiral polymer is performed with a halide of general formula $R_3X$, where X represents Cl, Br or I and $R_3$ is as defined above. $R_3$ can also be a functionalized group of the type $$Z-(CH_2)_n-$$

in which
n = 1 to 4
Z = I, CN, $CO_2R^4$ ($R^4$ = alkyl), $OR^5$ ($R^5$ = $CH_3$, tosyl, tetrahydropyranyl), Y—NH (Y = benzyloxycarbonyl, t-butyloxycarbonyl, $R^4S$,

The deprotonated derivative bonded to the chiral polymer or copolymer can also react:
in aldolization and ketolization reactions with $R^6CHO$ ($R^6$ = alkyl, aryl or aralkyl) and with aliphatic or arylaliphatic ketones,
in 1,4-addition reactions with acrylic esters, acrylonitrile or acrolein, thereby creating or recreating an asymmetric carbon-containing species.

According to an especially advantageous arrangement of this preferred embodiment of the process according to the present invention, the deprotonated derivative bonded to the chiral polymer is reacted with the halide $R_3X$ for 1 h to 4 h.

According to yet another embodiment of the present invention, an enantiomeric excess of more than 95% is produced when a chiral polymer containing one of the two isomers, R or S, according to the enantiomer excess desired, is chosen from a group of chiral units including N-acryloylprolinol.

In addition, compounds such as prochiral derivatives and enantiomers anchored to the support of the present invention in which the chiral unit can be N-acryloylprolinol, can thermo-dynamically equilibrate the intermediate enolates without the need to work at low temperatures such as —78C°.

The result is that, in contrast to the prior art processes which are carried out only at very low temperatures, of the order of —70° to —80° C., the process according to the present invention may be carried out entirely at room temperature, and that it is even possible, surprisingly, to improve its outcome by a step of heating the species having a reactive achiral portion, preferably at moderate temperatures, such as 60° to 70° C.

According to a preferred embodiment of the process according to the present invention, the asymmetric synthesis of amino acids on a support is performed at a temperature above 0° C.

According to another preferred embodiment of the process according to the invention, the derivative bonded to the polymer is heated to the refluxing temperature of tetrahydrofuran (67° C.) at the end of the first step for a period of 15 min to 4 h.

A summary example of a preferred embodiment of asymmetric synthesis is as follows:

65% (by weight) of the N-acryloyl derivative of an (S)-amine chosen from among prolinol methyl ether, N-methyl α-phenylethylamine, and prolinol, was copolymerized with 10% of N,N-dimethylethylenebisacrylamide as a cross-linking agent and 25% of N-acryloyl N-methyl p-aminobenzaldehyde as functionalizing agent. 10% cross-linking assures good mechanical properties for the support. Further, a loading of 1 meq of aldehyde function per gram was used. In this way, each aldehyde function is statistically surrounded by three to four chiral pendants. An idealized structure of the polymer, which was obtained in 90% yield, is shown in FIG. 2.

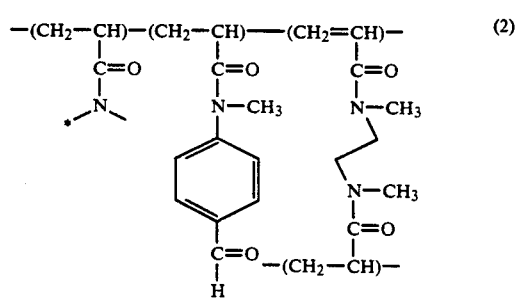

Acid-catalysed condensation of t-butyl glycinate with the above polymer (2) in the usual way afforded Schiff base (3).

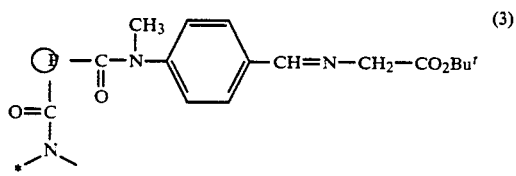

Deprotonation with LDA in THF gave an active asymmetric carbanion species (4).

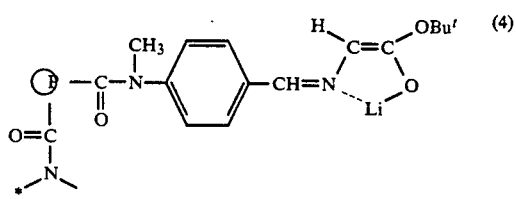

Subsequent reaction with an alkyl halide (R'X) followed by non-racemizing hydrolysis at room temperature with dilute HCl afforded the crude amino acid hydrochloride (5)

with quantitative recovery of polymer (2).

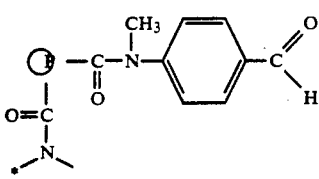

The crude amino acid (5) was reacted with hexamethyldisilazane (HMDS) to give the bis-trimethylsilyl derivative (6),

and then treated with an excess of methanol, to allow final isolation of the pure amino acid (7) with predominant (S)-configuration.

Conversely, utilization of (R)-pendants in step 1 will give rise to (R)-amino acids.

A further description of the application of the concept of supramolecular asymmetric induction to enantioselective protonation (or deracemization reaction) is as follows. Schiff bases (8)

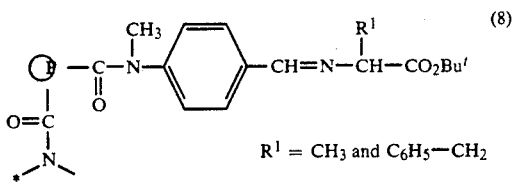

$R^1 = CH_3$ and $C_6H_5—CH_2$ were prepared by reacting copolymer (2 above) with racemic alanine and phenylalanine 5-butyl ester.

The following steps were routinely applied: deprotonation at −78° C. with LDA in THF, addition of water at the same temperature, hydrolysis at 20° C. with dilute HCl, and successive treatment with HMDS and methanol. The enantiomeric excesses for the (S)-prolinol methyl ether pendant are given in table 2 (entries 1 and 2). Yields of (7) ($R'$—$CH_3$ and $CH_2$—$C_6H_5$) amounted to 90%

TABLE 2

| Entry | Initial supported aminoacid | (7) ee% (R) |
|---|---|---|
| 1 | (R,S)—Phe | 49 |
| 2 | (R,S)—Ala | 55 |
| 3 | (R,S)—Ala | 11 |
| 4 | (R)—Ala | 100 |

(R)-Alanine and (R)-phenylalanine were predominantly formed with a (S)-pendant. As a result, both alkylation and protonation occurred preferentially from the same diastereotopic face of the ester enolates.

Unexpected results were obtained when the deracemization procedure was applied at −78° C. to each enantiomer of alanine. With (S)-Ala (entry 3), an 11% enantiomeric excess of (R)-Ala was formed; which means that a 55.5% inversion of the starting (S)-epimer had occurred, in good agreement with the value of entry 2. On the contrary, the (R)-Ala precursor was recovered unchanged (entry 4); however 90% incorporation of deuterium by treatment with LDA and D$_2$O proved that an ester enolate was an intermediate. Epimeric precursors thus give rise, in a kinetically controlled step, to non-identical enolates that behave differently with electrophiles.

The present invention will be better understood by means of the further description below, which relates to examples of preparation of the chiral support polymer, the functionalization agent and to examples of embodiments of the process for the asymmetric synthesis of amino acids according to the present invention.

The enantiomeric excesses (ee) are determined either by measurement of the optical rotations, or preferably using Marfey's reagent (Carlsberg Res. Comm., 1984, 49, 591) which permits separation of the diastereoisomers by reverse-phase HPLC with excellent precision.

As will be apparent from the examples which follow, the invention is in no way limited to those of its embodiments and methods of implementation and application which have just been described; it encompasses, on the contrary, all variants which may occur to the specialist in the field, without falling outside the scope or the range of the present invention. It should be clearly understood that the following examples are given only by way of illustration of the subject of the invention, and in no way constitute a limitation of the latter.

EXAMPLES

I. Preparation of a Chiral Support Polymer

Example 1

10.1 g (0.065 mole) of (R)- or (S)-N-acryloylprolinol, 1.3 g of bis(acryloyl)-N,N'-dimethylethylenediamine and 3.6 g (0.019 mole) of N-acryloyl-N-methyl-p-aminobenzaldehyde were added to 30 ml of tetrahydrofuran, followed by the addition of 1.5 g of azoisobutyronitrile. The mixture was heated for 1 h to reflux, cooled to room temperature and filtered. The product was washed successively with EtOH+10% of ether and with CH$_2$Cl$_2$+10% of ether. The residue was suspended in 50 ml of ether and the lumps were broken up with a spatula. The product was filtered off and dried under vacuum over P$_2$O$_5$ at room temperature. It was sieved between 0.08 mm. and 0.2 mm. Yield 90-95%.

The load, measured by oxime formation, was 1.1 meq CHO per gram.

Example 2

The same quantities of the three monomers utilized in Example 1 were dissolved in a 1:1 mixture of alcohol and water. After degassing with a sonic probe, a stream of nitrogen was bubbled through for 15 min. A solution of 0.3 g of ammonium persulfate in 1 ml of water was then added, followed, after homogenization, by the addition of 0.3 ml of tetramethyl-ethylenediamine. The mixture was homogenized and, after a few minutes, the temperature rises by 4° to 7° C.

The mixture was left for 1 h and filtered and the product was washed with acetone and alcohol. The resin was suspended in ether followed by the same procedure as in Example 1. Yield 90-95% after sieving. Load identical to that of Example 1.

Example 3

Paraffin oil (400 ml) and sorbitane trioleate (Fluka SPAN ® 85) (0.3 ml) were introduced into a 2-1 cylindrical reactor equipped with a stirrer and a nitrogen inlet. A strong stream of nitrogen was bubbled through for 30 minutes before the introduction of (R)- or (S)-N-acryloylprolinol (0.12 mole), bis(acryloyl)-N,N'-dimethyl-ethylenediamine (0.013 mole) and N TM acryloyl-N-methyl-p-aminobenzaldehyde (0.035 mole), these compounds being diluted in water (110 ml) and ethanol or dimethylformamide (110 ml). The mixture was stirred under a slow stream of nitrogen and the stirrer speed was adjusted until the suspended drops reached a diameter of about 0.1 mm. A solution of 0.5 g of ammonium persulfate in 1 ml of water was then added, followed by the addition of 0.36 ml of tetramethylethylenediamine. After a short induction period, the temperature rose to about 30° C. After 30 min, the mixture was diluted with petroleum ether. The polymer beads were collected on a Buchner covered with a nylon mesh (100 um), copiously washed successively with petroleum ether, acetone, aqueous acetone (1:1), water, ethanol and ether and finally dried under vacuum over $P_2O_5$ at room temperature. Yield 90–95% of resin beads (diameter between 0.1 and 0.2 mm). Load identical to that of Example 1.

II. Preparation of Functionalizing Agents

Example 4

N-Acryloyl N-methyl p-aminobenzaldehyde

A solution of acryloyl chloride (10.9 g, 0.12 mole) in 20 mL of anhydrous toluene was slowly added at $-5°$ C. to a stirred solution of N-methyl p-aminobenzadehyde (13.5 g, 0.10 mole) and of triethylamine (12.2 g, 0.12 mole) in 150 mL of anhydrous toluene. Stirring was continued for 12 hr at room temperature and the solution was evaporated under vacuum. The residual yellow oil was purified by chromatography on silica gel ($CH^2Cl^2$ as eluant).

Yield=95%, Rf ($CH^2Cl^2$)=0.44

NMR ($CDCl^3$) δppm: 3.43 (s, 3H, N—$CH^3$); 5.4–6.7 (m, 3H, $CH^2$=CH); 7.2–8.1 (1, 4H, Ar); 9.2 (s, 1H, CHO).

Analysis calc. for $C^{11}H^{11}NO^2$: C 69.82, H 5.86; found C 69.68, H 5.72.

Example 5

N-Acryloyl-N-methyl-α-phenylethylamine

This was performed according to the above procedure with N-methyl-α-phenyl ethylamine in place of N-methyl p-amino benzaldehyde. The residual oil was distilled. $Bp^1$=123°–125° C. Yield=95% $[α]=-227°$ (C-1.245, toluene) NMR ($CDCl^3$) δppm: 1.54 (d, 3H, $CH^3$); 2.74 (s, 3H, N—$CH^3$); 5.6–6.7 (m, 3H, $CH^2$=CH); 7.34 (s, 5H, Ar).

Analysis calc for $C^{12}H^{19}NO$: C 76.15, H 7.99, N 7.40; found C 76.37, H 7.83, N 7.20.

III. Asymmetric Synthesis of Amino Acids

Example 6

10 g of copolymer obtained in Examples 1, 2 or 3 from (S)-prolinol and 2.9 g of racemic t-butyl alaninate in 150 ml of toluene and a few drops of boron trifluoride etherate were heated to reflux, removing the water formed by means of a Dean and Stark trap. When the reaction was complete, the mixture was allowed to return to room temperature and the resin was filtered off, washed with dichloromethane and ether and dried under vacuum over $P_2O_5$ at room temperature.

To a stirred suspension of the Schiff's base thereby obtained, in 200 ml of anhydrous tetrahydrofuran, a solution of lithium diisopropylamide (50 moles) in 90 ml of tetrahydrofuran was added at room temperature. The mixture was heated for 2 h under reflux and cooled to 20° C., 40 ml of water was added and the mixture was left for 2 h. The resin was then filtered off and copiously washed successively with tetrahydrofuran, dichloromethane and anhydrous ether.

A suspension of the above resin in 200 ml of 1.5 N hydrochloric acid was stirred for 4 h at room temperature. The solid was filtered off and washed with 200 ml of water, and the filtrates were combined and concentrated to dryness under vacuum.

The residue of amino acid hydrochloride was stirred for 1 h with 10 ml of hexamethyldisilazane. The insoluble matter was filtered off and 20 ml of methanol were added to the filtrate; after 10 min, the solvent was evaporated off and the residue of (R)-alanine was dried under vacuum. Yield 95–97%; enantiomeric excess (determined by polarimetry) 96–98%.

The recovered resin can be recycled after drying.

Example 7

The same operation as in Example 6 was carried out with a polymer prepared from (R)-prolinol. (S)-Alanine was obtained with the same chemical yield and the same enantioselectivity.

Example 8

The same procedure as in Example 6 was carried out, but the whole deprotonation and reprotonation reaction was performed at $-78°$ C. (R)-Aniline was obtained with an ee=61%.

Example 9

The same operation as in Example 6 was carried out, but starting with t-butyl (RS)-valinate. (R)-Valine was obtained with a 95–97% yield and an ee=98–99%.

Example 10

The same operation as in Example 6 was carried out, but the supported Schiff's base was prepared from t-butyl glycinate. After formation of the enolate by the action of lithium diisopropylamide in tetrahydrofuran at 20°, the mixture was heated for 2 h under reflux and cooled to 20°, 15 moles of methyl iodide in 10 ml of tetrahydrofuran were added dropwise and the mixture was left for 2 h.

After treatment as described in Example 6, (S)-alanine was isolated with a 95–97% yield and an ee=98–99%.

Example 11

Same procedure as in Example 10, utilizing a copolymer prepared from (R)-prolinol. Under these conditions, (R)-alanine was isolated with the same yield and the same enantioselectivity as in Example 10.

Example 12

Same procedure as in Example 10, but the enolate was not brought to reflux. (S)-Alanine was obtained with an ee=82%.

Example 13

The same operation as in Examples 6 and 9 was carried out starting with t-butyl (RS)-phenylalaninate. (R)-Phenylalanine was obtained with a 95–97% yield and an ee>99%.

Example 14

The same operation as in Example 10 was carried out, but replacing methyl iodide by isopropyl iodide.

After treatment as described, (S)-valine was isolated with a 95–97% yield and an ee>99%.

Example 15

The same operation as in Example 10 was carried out, but replacing methyl iodide by benzyl bromide. (S)-Phenylalanine was isolated with a 95–97% yield and an ee>99%.

Example 16

The same operation as in Example 6 was carried out, but starting with t-butyl (S)-alaninate. (R)-Alanine was obtained with a quantitative yield and with an ee>99%.

Example 17

The same operation as in Example 6 was carried out, but utilizing the N-acryloyl derivative of (R)-methylbenzylamine as a chiral agent. Utilizing 5 equivalents of LDA, (R)-alanine was isolated with a 95% yield and an ee=86%. The ee fell to 37% when 1 equivalent of LDA was employed.

We claim:

1. A process for asymmetric synthesis comprising the steps of reversibly reacting (1) a prochiral derivative or (2) at least one enantiomer with a functionalizing unit of a support polymerized or copolymerized from at least one chiral unit, wherein said chiral unit may also be the source of said functionalizing unit or copolymerized from at least one chiral unit and at least one functionalizing unit;

converting the prochiral portion of said reacted prochiral derivative or the chiral portion of said enantiomer into a species having a reactive achiral portion;

creating, under conditions of thermodynamic equilibrium at a temperature of at least 20° C., an asymmetric carbon atom from the reactive achiral portion of said species; and separating a second species containing said asymmetric carbon atom from said support, wherein said second species is present in enantiomeric excess.

2. The asymmetric process of claim 1, wherein the enantiomeric excess of said asymmetric carbon-containing species is at least 85%.

3. The asymmetric process of claim 2, wherein said enantiomeric excess is at least 95%.

4. The asymmetric process of claim 3, wherein said enantiomeric excess is at least 99%.

5. The asymmetric process of claim 1 wherein said prochiral derivative is of the general formula (I)

$$H_2N-CH(CH_2)_nCOOR_2 \quad \text{(I)}$$
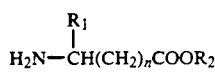

in which
n is equal to 0 or 1,
$R_1$ represents a hydrogen atom, and
$R_2$ represents a linear or branched $C_1$ to $C_5$ alkyl group or an aryl group.

6. The asymmetric process of claim 1, wherein said chiral unit comprises N-acryloylprolinol, prolinol methyl ether or prolinol, and wherein said chiral unit is in the R or S form.

7. The asymmetric process of claim 1, wherein said species having a reactive achiral portion is a carbanion.

8. The asymmetric process of claim 7, wherein said carbanion is an enol ester.

9. The asymmetric process of claim 7, wherein said carbanion is an enol ether.

10. The asymmetric process according to claim 1 for the asymmetric synthesis of amino acids, wherein said prochiral derivative is of the general formula:

$$H_2N-CH(CH_2)_nCOOR_2 \quad \text{(I)}$$

in which
n is equal to 0 or 1,
$R_1$ represents a hydrogen atom, and
$R_2$ represents a linear or branched $C_1$ to $C_5$ alkyl group or an aryl group,
and wherein:
in a first step, the prochiral portion of the prochiral derivative bonded to said support by reaction with the functionalizing unit of said support is deprotonated at room temperature with a strong base in an aprotic solvent to create a species having a reactive achiral portion;
in a second step, either alkylation or protonation of the deprotonated prochiral derivative bonded to the chiral polymer is performed, under conditions of thermodynamic equilibrium at a temperature of at least 20° C., to create an asymmetric carbon atom from the reactive achiral portion of the species; and
in a third step, a bond connecting a second species containing said asymmetric carbon atom to the support is cleaved by hydrolysis to obtain an amino acid of general formula:

$$H_2N-\underset{\underset{R_3}{|}}{\overset{\overset{R_1}{|}}{C}}-(CH_2)_nCOOH \quad \text{(II)}$$
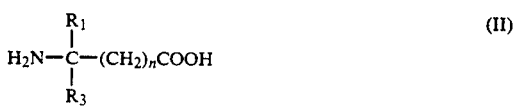

where $R_1$ and n are as defined above, $R_3$ represents an alkyl or aralkyl group, and $R_1$ and $R_3$ necessarily are different, wherein the amino acid is present in an enantiomeric excess.

11. The asymmetric process of claim 10, wherein said aprotic solvent is tetrahydrofuran.

12. The asymmetric process of claim 10, wherein said bond that is cleaved is a bond connecting said second species containing an asymmetric carbon atom to said functionalizing unit.

13. The asymmetric process of claim 12, wherein after said cleavage, the support is recovered and reused.

14. The asymmetric process of claim 12, wherein said bond that is cleaved is a double bond and the number of atoms in the shortest bonded path between said double bond and the chiral center of said second species containing an asymmetric carbon atom is at most equal to 5.

15. The asymmetric process of claim 14, wherein said number of atoms is at most 3.

16. The asymmetric process of claim 15, wherein said number of atoms is at most 2.

17. The asymmetric process of claim 1, wherein protonation of the deprotonated prochiral derivative is performed by adding water, an alcohol or an inorganic or organic acid.

18. The asymmetric process of claim 1, wherein alkylation of the deprotonated prochiral derivative is performed with a halide of general formula $R_3X$, where X represents Cl, Br or I and $R_3$ represents an alkyl or aralkyl group.

19. The asymmetric process of claim 1, wherein said asymmetric carbon atom is created at a temperature above 20° C.

20. The asymmetric process of claim 1, wherein said asymmetric carbon atom is created at a temperature above 60° C.

21. The asymmetric process of claim 1, wherein said asymmetric carbon atom is created at a temperature above 70° C.

22. The asymmetric process of claim 1, wherein said conditions of thermodynamic equilibrium occur at the refluxing temperature of tetrahydrofuran for a period of 15 min to 4 h.

23. The asymmetric process of claim 1, wherein the prochiral derivative is reversibly reacted with said functionalizing unit of said support by formation of a Schiff's base, an aldehyde stem, a halogenate or a hydroxyl group.

24. The asymmetric process of claim 1, wherein said conditions of thermodynamic equilibrium occur for a period of 15 minutes to 4 hours.

25. The asymmetric process of claim 24, wherein said conditions of thermodynamic equilibrium occur for a period of about 2 hours.

26. The asymmetric process of claim 1, wherein the bond formed when reversibly reacting said prochiral derivative or said at least one enantiomer with said functionalizing unit is cleavable by hydrolysis.

27. The process of claim 1, wherein said support is formed by the copolymerization of at least one said functionalizing unit, at least one said chiral unit and at least one cross-linking unit.

28. The asymmetric process of claim 1, wherein said enantiomers are of the general formula (I)

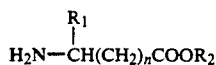
$$H_2N-CH(CH_2)_nCOOR_2 \quad (I)$$

in which
n is equal to 0 or 1,
$R_1$ represents an alkyl or aralkyl group, and
$R_2$ represents a linear or branched $C_1$ to $C_5$ alkyl group or an aryl group.

29. The asymmetric process according to claim 1 for the asymmetric synthesis of amino acids, wherein said enantiomer is of the general formula:
in which
n is equal to 0 or 1,
$R_1$ represents an alkyl or aralkyl group, and
$R_2$ represents a linear or branched $C_1$ to $C_5$ alkyl group or an aryl group,
and wherein:
in a first step, the chiral portion of the enantiomer bonded to said support by reaction with the functionalizing unit of said support is deprotonated at room temperature with a strong base in an aprotic solvent to create a species having a reactive achiral portion;
in a second step, either alkylation or protonation of the deprotonated enantiomer bonded to the chiral polymer is performed, under conditions of thermodynamic equilibrium at a temperature of at least 20° C., to create an asymmetric bond atom from the reactive achiral portion of the species; and
in a third step, a bond connecting a second species containing said asymmetric carbon to the support is cleaved by hydrolysis to obtain an amino acid of general formula:

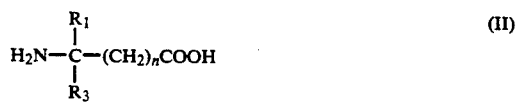
$$H_2N-\underset{\underset{R_3}{|}}{\overset{\overset{R_1}{|}}{C}}-(CH_2)_nCOOH \quad (II)$$

where $R_1$ and n are as defined above, $R_3$ represents an alkyl or aralkyl group, and $R_1$ and $R_3$ necessarily are different, wherein the amino acid is present in an enantiomeric excess.

30. The asymmetric process of claim 1 wherein said functionalizing unit is achiral.

31. The asymmetric process of claim 1, wherein said chiral unit contains an unsaturated bond.

32. A process for asymmetric synthesis comprising the steps of reversibly reacting (1) a prochiral derivative or (2) a mixture of enantiomers with an achiral functionalizing unit of a support polymerized or copolymerized from at least one chiral unit, wherein said chiral unit may also be the source of said functionalizing unit or copolymerized from at least one chiral unit and at least one functionalizing unit;
converting the prochiral portion of said reacted prochiral derivative or the chiral portion of said enantiomers into a species having a reactive achiral portion;
creating, under conditions of thermodynamic equilibrium at a temperature of at least 20° C., an asymmetric carbon atom from the reactive achiral portion of said species; and
separating a second species containing said asymmetric carbon atom from said support, wherein said second species is present in enantiomeric excess.

33. The asymmetric process of claim 32 wherein said functionalizing unit is achiral.

34. A process for asymmetric synthesis comprising the steps of reversibly reacting a prochiral derivative with a functionalizing unit of a support polymerized or copolymerized from at least one chiral unit, wherein said chiral unit may also be the source of said functionalizing unit or copolymerized from at least one chiral unit and at least one functionalizing unit; converting the prochiral portion of said reacted prochiral derivative into a species having a reactive achiral portion; creating, under conditions of thermodynamic equilibrium at a temperature of at least 20° C., an asymmetric carbon atom from the reactive achiral portion of said species; and separating a second species from said support, wherein said second species is present in enantiomeric excess.

35. The asymmetric process of claim 34, wherein said functionalizing unit is achiral.

36. A process for asymmetric synthesis comprising the steps of reversibly reacting a prochiral derivative or a mixture of enantiomers with a functionalizing unit of a copolymeric or polymeric support also containing at least one chiral unit, wherein said chiral unit is selected from prolinol, prolinol methyl ether, N-acryloylprolinol, 1-amino-1-phenylethanes, 1-(N-alkylamino)-2-alkoxypropane, 1-pyrrolidinyl-2-methylpyrrolidine, N-methylalpha-phenylethylamine, methylbenzylamine and 1-amino-1-alkyl-2-hydroxyethane;

converting the prochiral portion of said reacted prochiral derivative of the chiral portion of each of said enantiomers into a species having a reactive achiral portion;

creating, under conditions of thermodynamic equilibrium at a temperature of at least 20° C., an asymmetric carbon atom from the reactive achiral portion of said species; and separating a second species containing said asymmetric carbon atom from said copolymeric or polymeric support, wherein said second species is present in enantiomeric excess.

37. The asymmetric process of claim 1, wherein said functionalizing unit is achiral.

38. A process for producing an excess of enantiomers comprising the steps of reversibly reacting a starting material selected from a prochiral derivative, a mixture of enantiomers or a substantially optically pure enantiomer with at least one functionalizing unit of a support obtained by (1) the copolymerization of at least one chiral unit and at least one functionalizing unit of (2) the polymerization or copolymerization of at least one chiral unit which is also the source of said functionalizing unit;

creating a species having a reactive achiral portion;

creating, under conditions of thermodynamic equilibrium at a temperature of at least 20° C., an asymmetric carbon atom from the reactive achiral portion of said species; and separating a second species containing said asymmetric carbon atom from said copolymeric or polymeric support, wherein said second species is present in enantiomeric excess.

39. The process of claim 38, wherein said chiral unit and said functionalizing unit polymerized or are copolymerized in a first step, followed by cross-linking in the presence of at least one cross-linking unit.

40. The process of claim 38, wherein said chiral unit and said functionalizing unit are copolymerized in the presence of at least one crosslinking unit.

41. The process of claim 38, wherein said functionalizing unit is achiral.

42. A process for producing an excess of enantiomers comprising the steps of reversibly reacting a starting material selected from a prochiral derivative, a mixture of enantiomers or a substantially optically pure enantiomer with at least one functionalizing unit of a support obtained by the polymerization or copolymerization of at least one chiral unit which is also the source of a functionalizing unit;

creating a species having a reactive achiral portion;

creating, under conditions of thermodynamic equilibrium at a temperature of at least 20° C., an asymmetric carbon atom from the reactive achiral portion of said species; and separating a second species containing said asymmetric carbon atom from said polymeric or copolymeric support, wherein said second species is present in enantiomeric excess.

43. The process of claim 42, wherein said chiral unit which is a source of said functionalizing unit is polymerized or copolymerized in a first step, followed by crosslinking in the presence of at least one crosslinking unit.

44. The process of claim 42, wherein said chiral unit which is a source of said functionalizing unit is copolymerized in the presence of at least one crosslinking unit.

45. A process for deracemization comprising the steps of reversibly reacting a racemic mixture of enantiomers with at least two functionalizing units of a copolymeric support obtained by the copolymerization of at least one chiral unit with at least one functionalizing unit or a polymeric or copolymeric support obtained by the polymerization or copolymerization of at least one chiral unit which is also the source of said functionalizing unit;

converting the chiral portion of each of said enantiomers reacted with each of said functionalizing units into a species having a reactive achiral portion;

creating, under conditions of thermodynamic equilibrium at a temperature of at least 20° C., an asymmetric carbon atoms from the reactive achiral portion of said species; and separating a second species containing an asymmetric carbon atom from said copolymeric or polymeric support, wherein said second species is present in enantiomeric excess.

46. The deracemization process of claim 45, wherein said chiral unit and said functionalizing unit are copolymerized in the presence of at least one crosslinking unit.

47. The deracemization process of claim 46, wherein said conditions of thermodynamic equilibrium occur for a period from 15 min to 4 h.

48. The deracemization process of claim 47, wherein the enantiomeric excess of said second species is at least 85%.

49. The deracemization process of claim 48, wherein the enantiomeric excess of said species is at least 95%.

50. The deracemization process of claim 49, wherein the enantiomeric excess of said second species is at least 99%.

51. The deracemization process of claim 45, wherein the bond formed by reversibly reacting each enantiomer with a functionalizing unit is cleavable by hydrolysis.

52. The deracemization process of claim 45, wherein each of said functionalizing units is achiral.

53. The process for deracemization comprising the steps of reversibly reacting a racemic mixture of enantiomer with at least two functionalizing units of a copolymeric or polymeric support also containing at least one chiral unit, wherein said chiral unit is selected from prolinol, prolinol methyl ether, N-acryloylprolinol, 1-amino-1-phenylethanes, 1-(N-alkylamino)-2-alkoxypropane, 1-pyrrolidinyl-2-methylpyrrolidine, N-methyl-alphaphenylethylamine, methylbenzylamine and 1-amino-1-alkyl-2-hydroxyethane;

converting the chiral portion of each of said reacted enantiomers into a species having a reactive achiral portion;

creating, under conditions of thermodynamic equilibrium at a temperature of at least 20° C., an asymmetric carbon atom from the reactive achiral portion of said species; and separating a second species containing said asymmetric carbon atom from said copolymeric or polymeric support, wherein said second species is present in enantiomeric excess.

54. The deracemization process of claim 53, wherein each of said functionalizing units is achiral.

55. A process for inversion of enantiomeric configuration comprising the steps of reversibly reacting an enantiomer of arbitrary configuration with a functionalizing unit of a copolymeric support obtained by the copolymerization of at least one chiral unit with at least one functionalizing unit or a polymeric or copolymeric support obtained by the polymerization or copolymerization of at lest one chiral unit which is a source of said functionalizing unit;

converting the chiral portion of said enantiomer reacted with said functionalizing unit into a species having a reactive achiral portion;

creating, under conditions of thermodynamic equilibrium at a temperature of at least 20° C., an asymmetric carbon atom from the reactive achiral portion of said species; and separating a second species containing said asymmetric carbon atom from said copolymeric or polymeric support, wherein said second species is present in an enantiomeric excess and wherein said second species is an enantiomer having a configuration opposite to that of said enantiomer of arbitrary configuration.

56. The inversion process of claim 55, wherein said chiral unit and said functionalizing unit are copolymerized in the presence of at least one crosslinking unit.

57. The inversion process of claim 56, wherein said conditions for thermodynamic equilibrium occur for a period from 15 min to 4 h.

58. The inversion process of claim 56, wherein the enantiomeric excess of said second species is at least 85%.

59. The inversion process of claim 58, wherein the enantiomeric excess of said second species is at least 95%.

60. The inversion process of claim 59, wherein the enantiomeric excess of said second species is at least 99%.

61. The inversion process of claim 55, wherein the bond formed by reversibly reacting said enantiomer of arbitrary configuration with a functionalizing unit is cleavable by hydrolysis.

62. The inversion process of claim 55, wherein said functionalizing unit is achiral.

63. A process for inversion of enantiomeric configuration comprising the steps of reversibly reacting an enantiomer of arbitrary configuration with a functionalizing unit of a copolymeric or polymeric support also containing at least one chiral unit, wherein said chiral unit is selected from prolinol, prolinol methyl ether, N-acryloylprolinol, 1-amino-1-phenylethanes, 1-(N-alkylamino)-2-alkoxypropane, 1-pyrrolidinyl-2-methylpyrrolidine, N-methylalpha-phenylethylamine, methylbenzylamine and 1-amino-1-alkyl-2-hydroxyethane;

converting the chiral portion of said reacted enantiomer into a species having a reactive achiral portion;

creating, under conditions of thermodynamic equilibrium at a temperature of at least 20° C., an asymmetric carbon atom from the reactive achiral portion of said species; and separating a second species containing said asymmetric carbon atom from said copolymeric or polymeric support, wherein said second species is present in enantiomeric excess and wherein said second species is an enantiomer having a configuration opposite to that of said enantiomer of arbitrary configuration.

64. The inversion process of claim 63, wherein said functionalizing unit is achiral.

* * * * *

UNITED STATES PATENT AND TRADEMARK OFFICE
CERTIFICATE OF CORRECTION

PATENT NO. : 5,281,750
DATED : January 25, 1994
INVENTOR(S) : Robert Jacquier et al.

It is certified that error appears in the above-indentified patent and that said Letters Patent is hereby corrected as shown below:

Claim 17, column 17, line 3, change "1" to --10--.

Claim 18, column 17, line 7, change "1" to -10--.

Claim 29, column 17, line 58, after "formula" insert
-- 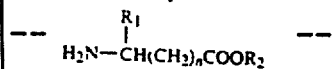 -- column 18, line 7, change "bond" to --carbon--.
       column 18, line 10, after "carbon" insert --atom--.

Claim 37, column 19, line 20, change "1" to "36".

Claim 38, column 19, line 28, change "of" to --or--.

Claim 39, column 19, line 42, delete "polymerized or" and insert --polymerized or-- after "are".

Claim 45, column 20, line 20, change "atoms" to --atom--.

UNITED STATES PATENT AND TRADEMARK OFFICE
CERTIFICATE OF CORRECTION

PATENT NO. : 5,281,750
DATED      : January 25, 1994
INVENTOR(S): Robert Jacquier et al.

It is certified that error appears in the above-indentified patent and that said Letters Patent is hereby corrected as shown below:

Claim 53, column 20, line 46, change "The"(1st occurence) to --A--.

Claim 53, column 20, lines 47 and 48, change "enantiomer" to --enantiomers--.

Claim 57, column 21, line 28, delete "for" after conditions and insert --of-- .

Signed and Sealed this

Ninth Day of May, 1995

Attest:

BRUCE LEHMAN

*Attesting Officer*          *Commissioner of Patents and Trademarks*